(12) United States Patent
Stark et al.

(10) Patent No.: US 7,986,399 B2
(45) Date of Patent: Jul. 26, 2011

(54) PORTABLE SAMPLE PREPARATION AND ANALYSIS SYSTEM FOR MICRON AND SUB-MICRON PARTICLE CHARACTERIZATION USING LIGHT SCATTERING AND ABSORPTION SPECTROSCOPY

(75) Inventors: Peter C. Stark, Los Alamos, NM (US); Eduardo Zurek, Barranquilla (CO); Jeffrey V. Wheat, Fort Walton Beach, FL (US); John M. Dunbar, Santa Fe, NM (US); Jose A. Olivares, Los Alamos, NM (US); Luis H. Garcia-Rubio, Temple Terrace, FL (US); Michael D. Ward, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 715 days.

(21) Appl. No.: 11/877,136

(22) Filed: Oct. 23, 2007

(65) Prior Publication Data
US 2009/0103086 A1 Apr. 23, 2009

(51) Int. Cl.
*G01N 1/00* (2006.01)
(52) U.S. Cl. .......................................... 356/36; 356/38
(58) Field of Classification Search ............. 356/36, 356/38; 422/62–67; 436/177–178
See application file for complete search history.

(56) References Cited

U.S. PATENT DOCUMENTS

| 3,902,971 | A | * | 9/1975 | Fletcher et al. ................. 356/36 |
| 4,395,493 | A | * | 7/1983 | Zahniser et al. ................ 356/38 |
| 5,830,359 | A | * | 11/1998 | Knight et al. ................. 436/178 |
| 5,907,108 | A | | 5/1999 | Garcia-Rubio et al. |
| 6,788,394 | B1 | | 9/2004 | Garcia-Rubio et al. |
| 6,984,526 | B2 | | 1/2006 | Garcia-Rubio et al. |
| 7,027,134 | B1 | | 4/2006 | Garcia-Rubio et al. |
| 2004/0259266 | A1 | * | 12/2004 | Barringer, Jr. ................ 422/67 |
| 2005/0233439 | A1 | | 10/2005 | Everhart et al. |
| 2006/0257854 | A1 | | 11/2006 | McDevitt et al. |
| 2008/0167198 | A1 | * | 7/2008 | Cooney et al. ................ 436/178 |

OTHER PUBLICATIONS

Patent Cooperation Treaty, Notification of Transmittal of the International Search Report and the Written Opinion of the International Searching Authority or the Declaration, 7 pps, mailed Jun. 22, 2009.

* cited by examiner

*Primary Examiner* — Kara E Geisel
(74) *Attorney, Agent, or Firm* — Husch Blackwell LLP (57) ABSTRACT

There is provided a method and device for remote sampling, preparation and optical interrogation of a sample using light scattering and light absorption methods. The portable device is a filtration-based device that removes interfering background particle material from the sample matrix by segregating or filtering the chosen analyte from the sample solution or matrix while allowing the interfering background particles to be pumped out of the device. The segregated analyte is then suspended in a diluent for analysis. The device is capable of calculating an initial concentration of the analyte, as well as diluting the analyte such that reliable optical measurements can be made. Suitable analytes include cells, microorganisms, bioparticles, pathogens and diseases. Sample matrixes include biological fluids such as blood and urine, as well as environmental samples including waste water.

18 Claims, 7 Drawing Sheets

PORTABLE SAMPLE PREPARATION AND ANALYSIS SYSTEM FOR MICRON AND SUB-MICRON PARTICLE CHARACTERIZATION USING LIGHT SCATTERING AND ABSORPTION SPECTROSCOPY

STATEMENT REGARDING FEDERAL RIGHTS

This invention was made with government support under Contract No. DE-AC52-06NA25396 awarded by the U.S. Department of Energy. The government has certain rights in the invention.

BACKGROUND OF INVENTION

Preparation of Cell Cultures for Spectroscopic Measurements Generally Involves Separation of the organisms from interfering, light absorbing matrixes. Cell culture preparation typically involves time consuming, labor intensive cell-washing processes and centrifugations. These processes are repeated until the interference from growth media and other interfering materials is adequately reduced to allow reliable spectroscopic measurements. Conventional sample preparation processes expose the cells to large changes in osmotic gradients, often causing the cells to lyse, resulting in poor spectroscopic data.

In addition to cell cultures, sample preparation for on-site analysis for disease and waterborne pathogens is also limited by conventional preparation methods and bulky experimental set-ups. There is therefore a need for a self-contained device capable of remote preparation and spectrometric analysis of a sample.

SUMMARY OF INVENTION

An illustrative aspect of the present invention is a filtration module device comprising sampling means for introducing a sample solution into the device, the sample solution containing an analyte and interfering particulate matter, wherein the particulate matter is smaller in size than the analyte; integral filtering means sized to segregate the analyte by preventing the analyte from passing through the filter while allowing the interfering particulate matter to pass through the filter; diluting means for introducing a diluent into the device to mix with the segregated analyte to form an analyte suspension for analysis; spectrometer means to analyze the analyte suspension; processing unit and software adapted to control the sampling means, diluting means and spectrometer means; and a waste removal means to remove the sample solution, diluent and analyte suspension from the device.

Another illustrative aspect of the present invention is a method for identifying analytes, the method comprising introducing a sample solution containing an analyte and interfering particulate matter, wherein the particulate matter is smaller in size than the analyte; integrally filtering the sample to segregate the analyte from the interfering particulate matter; forming a suspension of the analyte in a diluent; and analyzing the analyte with a spectrometer.

DETAILED DESCRIPTION

There is provided a method and device for remote sampling, preparation and optical interrogation of a sample using light scattering and light absorption methods. The device utilizes multi-wavelength spectroscopy, which can rapidly provide quantitative information for the detection and identification of many types of particles. A typical multi-wavelength spectrum provides information about the chemical composition, size, internal structure, and number of particles present in a sample. A multi-wavelength spectrum is generated from the combined absorption and scattering characteristics of the sample.

The device is a filtration-based device, or filtration module, that removes interfering background particle material from the sample matrix, by segregating or filtering the chosen analyte from the sample solution or matrix while allowing the interfering background particles to be pumped out of the device. The segregated analyte is then suspended in a diluent for analysis. The device is capable of calculating an initial concentration of the analyte, as well as diluting the analyte such that reliable optical measurements can be made. Suitable analytes include, but are not limited to, cells, microorganisms, bioparticles, pathogens and diseases. Sample matrixes include biological fluids such as blood and urine, cultured organisms and environmental samples including waste water.

Figure 1:
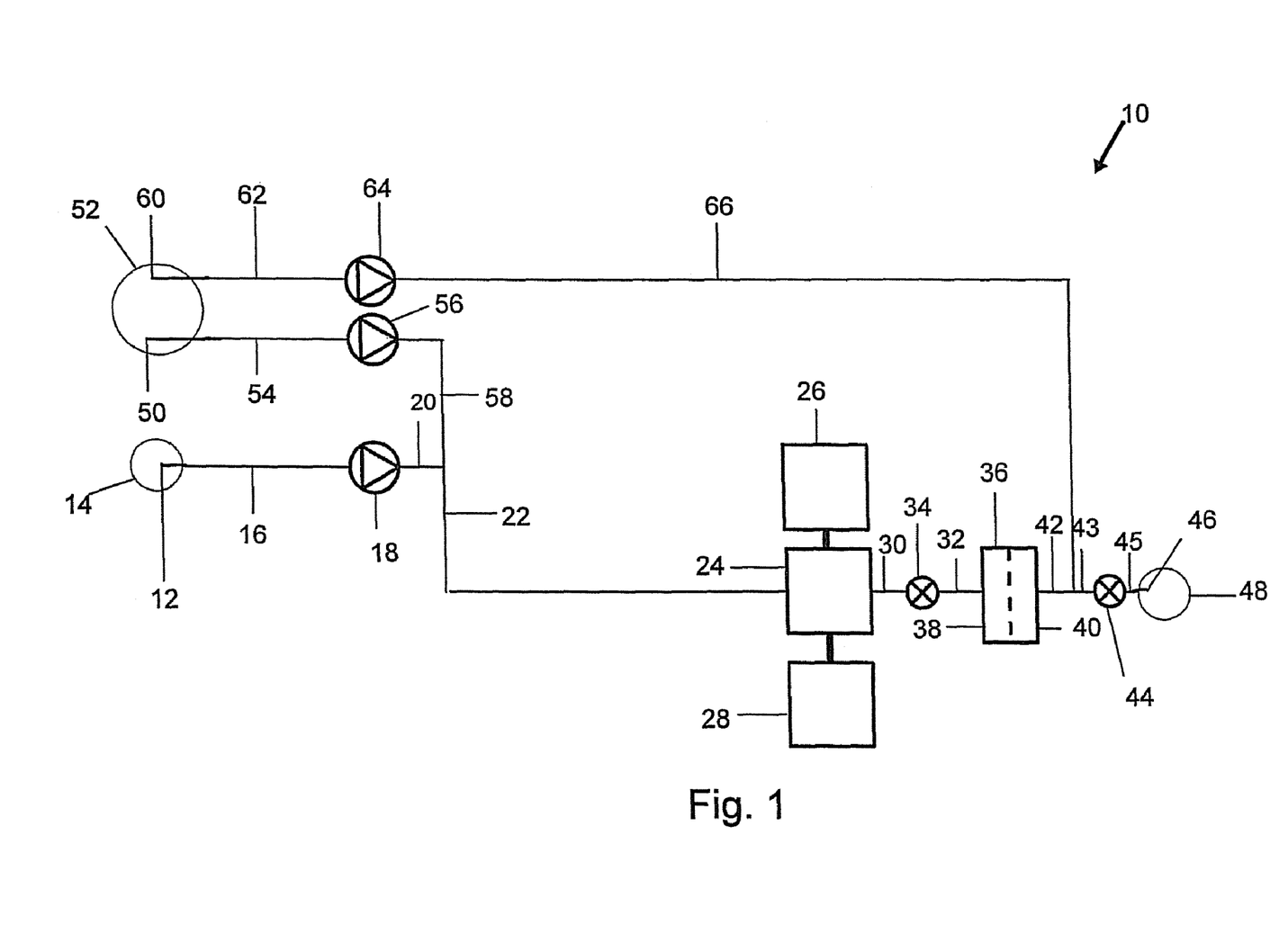
FIG. 1 is a schematic of a first embodiment of the filtration module device of the present invention.

A first illustrative embodiment of the present invention is seen in FIG. 1. The device 10 has a sample inlet port 12 which is in fluid communication with, and may be physically connected to a sample container 14. Tubing 16 connects the sample inlet port 12 to a pump 18. The tubing may be any suitable commercially available non-interfering tubing, such as that available from Bio-Chem, Inc., and the pump may be any suitably sized peristaltic pumping device. Tubing 20, 22 connects pump 18 to a quartz flow cell 24. The flow cell 24 is optically connected to a UV-VIS light source 26 and a spectrometer 28. Any commercially available spectrometer may be used, for example, an Ocean Optic HR Spectrometer. The light source typically emits light from about 180 to about 920 nanometers. Tubing 30, 32 and a valve 34 connect flow cell 24 to a filter 36 having a first side 38 and a second side 40. A suitable filter for the examples given herein is a 0.45 micrometer filter, but can be of any size suitable for recovering a specific analyte. Tubing 42, 43 connects the filter 36 to a valve 44, and tubing 45 connects valve 44 to a waste outlet 46 and an optional waste container 48.

A first diluent inlet port 50 is in fluid communication with and preferably connected to a diluent container 52. The diluent is typically deionized water, but can be any diluent suitable for the particular analyte, for example a buffered solution. Tubing 54 connects port 50 to a pump 56. Tubing 58 connects pump 56 to tubing 22 through a t-connector, not shown. Tubing 22 puts the first diluent inlet port in fluid communication with the flow cell 24 and filter 36, as discussed above.

A second diluent inlet port 60 is in fluid communication with and preferable connected to the diluent container 52, and further to a pump 64 through tubing 62. Pump 64 is connected to tubing 42, 43 through tubing 66 by a t-connector, not shown, placing the second diluent inlet port in fluid communication with the filter 36 and flow cell 24, as discussed above.

The device 10 is connected to software adapted to operate the pumps and valves in the desired sequence. The software is further adapted to analyze the data gathered by the spectrometer. Suitable commercially available software includes Lab-VIEW software, the use of which is well known in the art.

The method of the present invention allows remote sampling, sample preparation and optical analysis. Generally, the method involves drawing or pumping a sample solution to be analyzed into the device and integrally segregating the analyte by filtering the analyte out of the sample solution while allowing any smaller, interfering particles to be flushed out of the device. The analyte is then suspended in a diluent at the proper concentration for optical analysis by the spectrometer.

More specifically, an illustrative, non-limiting embodiment of the present method is described utilizing the embodiment illustrated in FIG. 1, described above. In the first step, a sample solution is drawn from sample container 14 through inlet 12 and tubing 16 by pump 18. The sample is further pumped through tubing 20, 22 into flow cell 24 and tubing 30. Valve 34 is in the closed position to allow a preliminary concentration analysis of the sample solution by spectrometer 28. Once the initial analysis is complete, valve 34 is opened, and the sample solution is pumped through tubing 32 and filter 36. The filter 36 is sized so that the analyte cannot pass through. The analyte is segregated from the sample solution by trapping it on the first side 38 of filter 36, while the smaller, interfering particles proceed through filter 36, tubing 42 and open valve 44, to waste outlet 46 and waste container 48. Once sufficient analyte has been collected by filter 36, pump 18 is turned off.

In an optional washing step, diluent is pumped from the diluent container 52 through first diluent inlet port 50 and tubing 54 by pump 56. The diluent continues to flow through tubing 58, 22, flow cell 24, tubing 30, 32 and open valve 34. The diluent flows through filter 36, washing the analyte trapped on the first side 38 of filter 36. The diluent, including any matter washed from the trapped cells, continues through tubing 42, 43, open valve 44 and tubing 45 to waste outlet 46 and waste container 48. Once washing is complete, pump 56 is turned off.

An analyte suspension forming step begins by closing valve 44. Diluent is pumped from diluent container 52 into second diluent inlet port 60 and tubing 62 by pump 64. Diluent continues through tubing 66 into tubing 42. As the diluent flows through filter 36, in the opposite direction from the flow of the sample solution and the diluent in the washing step, traveling from the second side 40 to the first side 38, the trapped analyte is mixed with and suspended in the diluent.

The diluent/analyte solution is then pumped through tubing 30, 32 and valve 34 into flow cell 24 for analysis by the spectrometer 28.

Figure 2:
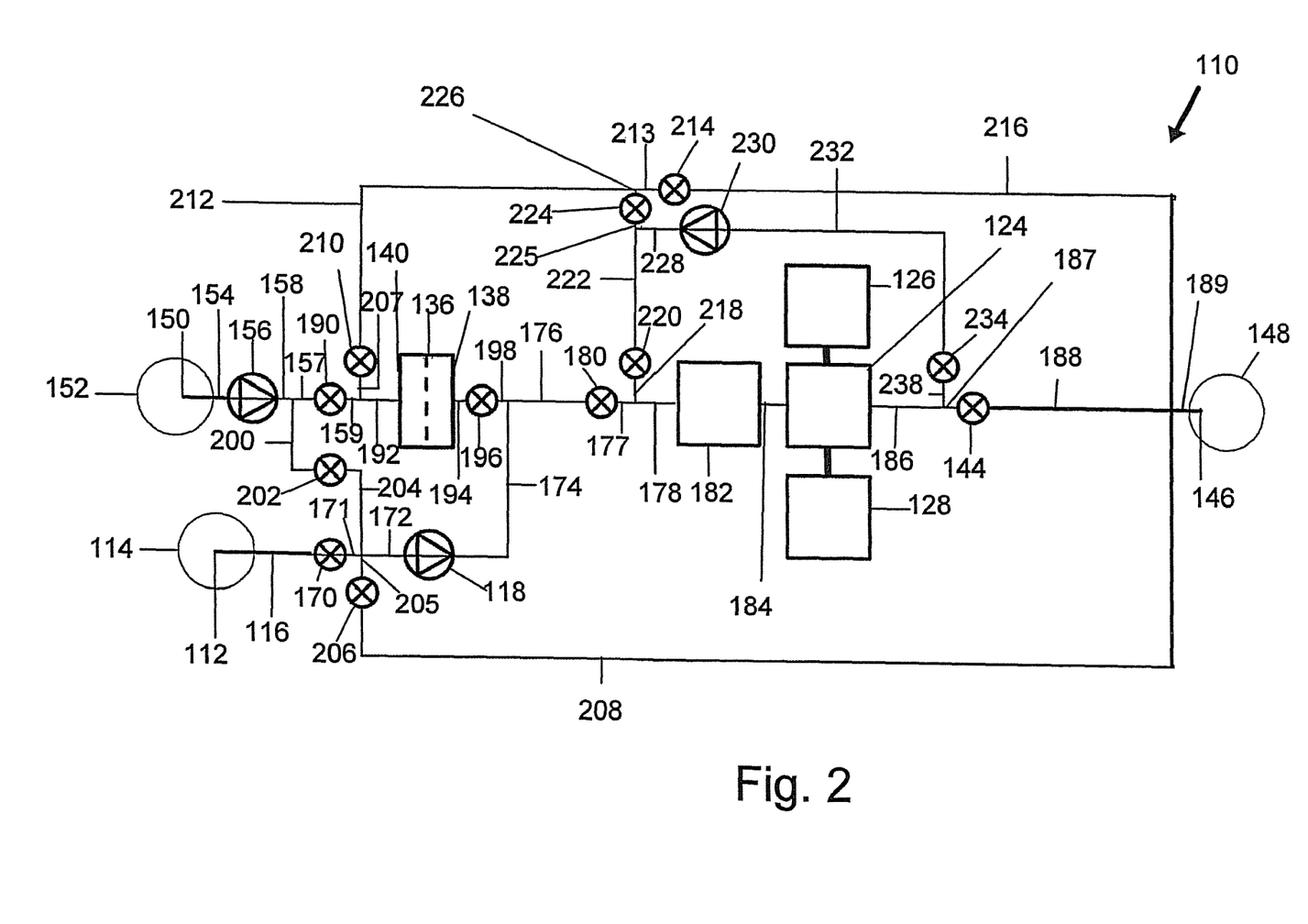
FIG. 2 is a schematic of a second embodiment of the filtration module device of the present invention.

A second illustrative, non-limiting embodiment of the present invention is shown in FIG. 2. Sample inlet port 112 is in fluid communication with and may be physically connected to a sample container 114 through tubing 116 which is also connected to a valve 170. Tubing 171, 172 connects valve 170 to pump 118, which is in fluid communication, through tubing 174, 176, 177, 178 and a valve 180 with mixing chamber 182. Mixing chamber 182 may be any conventional mixer, preferably a turbulence type mixing chamber.

Mixing chamber 182 is connected by tubing 184 to flow cell 124, which is optically connected to a UV-VIS light source 126 and a spectrometer 128. Tubing 186, 187, 188, 189 and valve 144 connect the flow cell 124 to waste outlet port 146 and optional waste container 148.

Diluent inlet port 150 and optional diluent container 152 are connected to pump 156 by tubing 154. Tubing 158, 159, 192 and valve 190 lead to filter 136, having a first side 138 and a second side 140. Valve 196 and tubing 194, 198 connect to tubing 176 through a t-connector, not shown. Tubing 192 is further connected through a t-connector, not shown, to tubing 207, 212, 213, 216 and valves 210, 214, which are in fluid communication with waste outlet port 146 through a t-connector (not shown) and tubing 189. Tubing 158 is connected through a t-connector, not shown, to tubing 200, 204 and valve 202 connecting to tubing 171, 172 and 205, through a 4-way connector, not shown. Tubing 205, 208 and valve 206 are connected to waste outlet port 146 through the t-connector (not shown) and tubing 189.

A recirculation loop is formed by tubing 218, connected by a t-connector, not shown, to tubing 177, 178, in combination with tubing 222, 228, 232, 238, valves 220, 234 and a pump 230. Tubing 222 is further connected by a t-connector, not shown, to tubing 225, valve 224 and tubing 226, further connected to tubing 212, 213 through a t-connector, not shown.

In an illustrative, non-limiting embodiment of a method of using the embodiment of FIG. 2, the sequence begins with all valves closed and all pumps off. To measure the concentration of the unfiltered sample, valves 170, 180, 144 are opened, and pump 118 is turned on. This allows the sample to travel into the sample inlet port 112, through tubing 116, 171, 172, and valve 170, to reach pump 118. Tubing 174, 176, 177, 178 and valve 180, lead the sample into the mixing chamber 182. Tubing 184 leads the sample to the flow cell 124, and tubing 186, 188 and valve 144 direct the sample solution out of the device through tubing 188, 189 and waste outlet 146. Sample concentration is measured by spectrometer 128 and analyzed by the associated software.

In a flow cell cleaning step, valves 202, 180, 220, 234, 144 are opened, and pumps 118, 156, 230 are turned on. Diluent is drawn through diluent inlet port 150 and tubing 154 by pumps 156, 118. The diluent continues through tubing 200, 204, 172, 174, 176, 177, 178 and valves 202, 180 until reaching mixing chamber 182. Tubing 184 directs the diluent into flow cell 124 to flush and clean the flow cell. Tubing 186, 187, 188, 189 and valve 144 lead the diluent to exit the device at waste outlet port 146. The diluent is further cycled through the recirculation loop by pump 230 through tubing 238, 232, 228, 222, 218 and valves 234, 220.

A sample capture step is initiated by opening valves 170, 196, 210, 214 and turning on pump 118. Pump 118 draws the sample solution through sample inlet port 112 and tubing 116, 171, 172, 174 198, 194 through open valves 170, 196. As the sample solution travels through the filter 136, the analyte is trapped on the first side 138 of the filter. The filtrate solution continues through tubing 192, 207, 212, 213, 216 and valves 210 and 214 until it exits the device at waste outlet port 146 though tubing 189.

In an analyte washing step, valves 202, 196, 210, 220, 224, 144 are opened, and pumps 156, 118 are turned on. Diluent is pumped in through inlet port 150, tubing 154, 158, 200, 204, 172, 174, 198 and 194 through open valves 202 and 196 by pumps 156, 118. As the diluent flows through filter 136, it washes the analyte trapped on the first side 138 of filter 136. The diluent then flows through tubing 192, 207, 212, 226, 225, 222, 218, 178 and valves 210, 224, 220 into mixing chamber 182, tubing 184, flow cell 124, tubing 186, 188, 189, valve 144 and exits the device through waste outlet port 146.

An analyte suspension forming step is necessary prior to introducing the segregated analyte into the flow cell for analysis. In this step, valves 190, 196, 180, 144 are opened and pump 156 is turned on. Diluent is pumped through inlet port 150, tubing 154, 158, 157, 159, 192 and valve 190 by pump 156. The diluent flows through filter 136 from the second side 140 to the first side 138, a direction opposite that of the sample capture and analyte washing steps. The diluent stream forces the analyte trapped on the second side 140 of filter 136 to be mixed with and suspended in the diluent forming an analyte suspension. The analyte suspension flows through tubing 194, 198, 176, 177, 178 and valves 196, 180 where the analyte suspension enters mixing chamber 182 for further mixing. The analyte suspension then travels through tubing 184 into flow cell 124 for analysis. The analyte suspension continues through tubing 186, 187, 188, 189 and valve 144 to exit the device at waste outlet 146.

In a recirculation step, valves 220, 234 are opened and pump 230 is turned on. The analyte suspension is circulated by pump 230 through the flow cell 124 and mixing chamber 182 through tubing 186, 238, 232, 228, 222, 218, 178, 184, and through open valves 220, 234.

The sample may be diluted by opening valves 202, 180, 144 and turning pumps 156, 118 on. Diluent is pumped through inlet port 150, through tubing 154, 158, 200, 204, 172, 174, 176, 177, 178, 184, mixing chamber 182, flow cell 124, tubing 186, 188, 189 and out waste outlet port 146. By keeping valves 220, 224, 234 closed, the analyte suspension in the recirculation loop, as described above, remains trapped in tubing 222, 228, 232. All valves except 220 and 234 are closed and pump 230 is turned on. The analyte suspension trapped in the recirculation loop and the diluent in tubing 178, 184, 186, mixing chamber 182 and flow cell 124 all circulate together to dilute the analyte suspension for analysis by spectrometer 128. The dilution step may be repeated until the analyte suspension is of a suitable concentration for absorption and light scattering spectroscopy.

A system cleaning step is performed by turning all pumps on and opening all valves except 170 and 202 to flush diluent throughout the system and out the waste outlet port 146. The filter 36 should be replaced after multiple analyses, or when a different analyte is to be analyzed.

In an alternate embodiment, a second filter, not shown, may be added to remove particulate matter that is larger than the cells to be analyzed. The filter is sized to let the analyte flow through the filter, while filtering out larger interfering particles from the sample solution. The second filter should be located upstream of the first filter 36.

Figure 3:
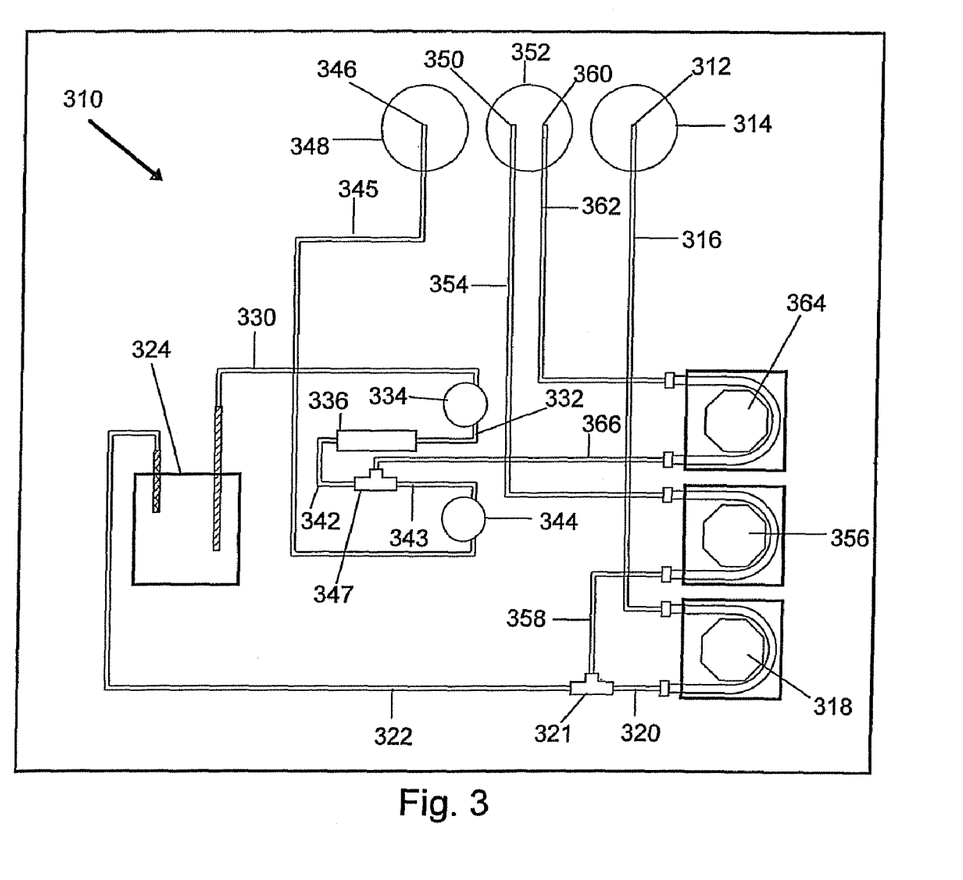
FIG. 3 is an illustration of a pump and valve set up of the first embodiment of the filtration module device of FIG. 1.
Figure 4:
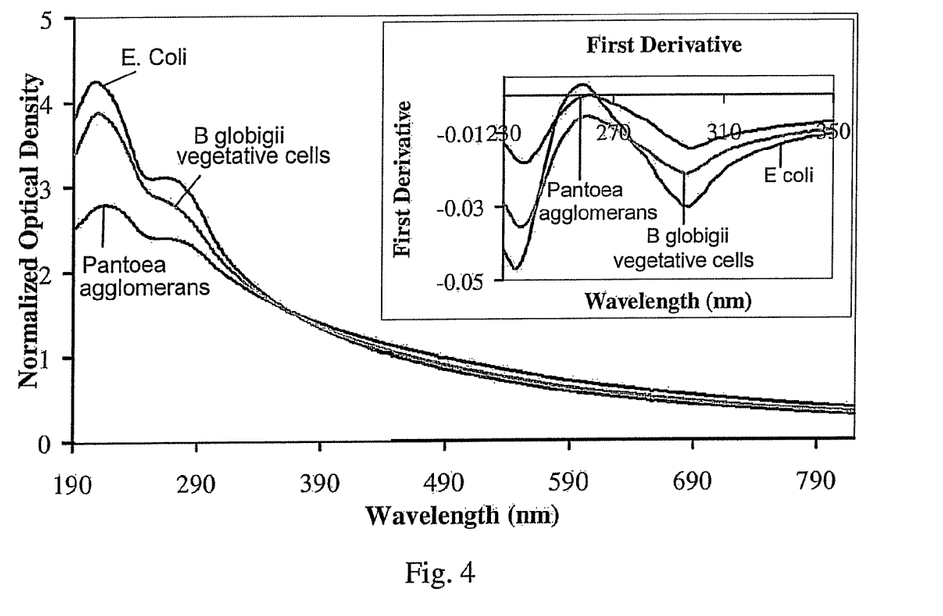
FIG. 4 is a graph of raw optical spectra generated by the device of the present invention analyzing samples of *E. coli, P. agglomerans* and *B. globigii* vegetative cells, as well as the first derivative of the raw optical spectra.
Figure 5:
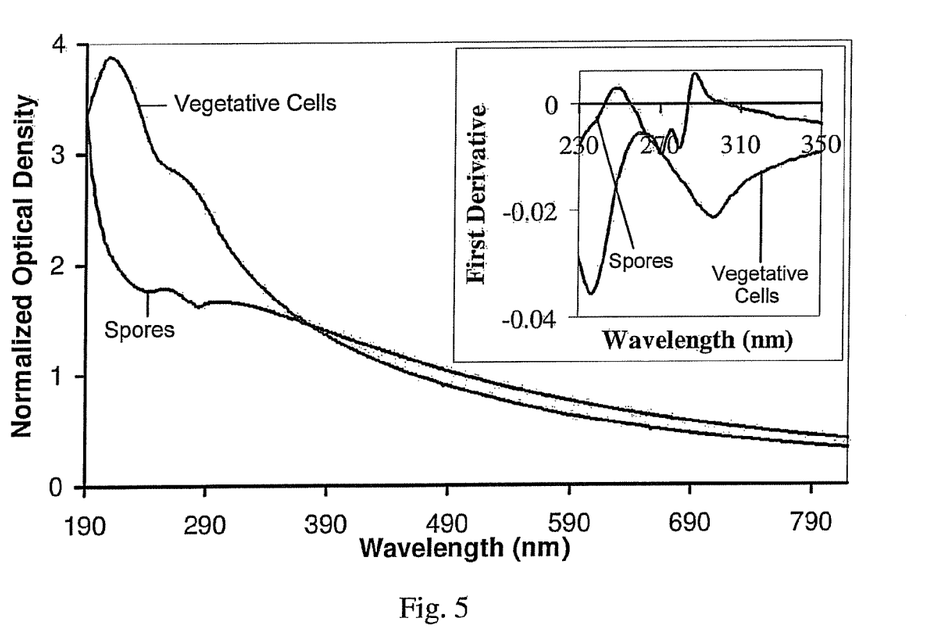
FIG. 5 is a graph of raw optical spectra generated by the device of the present invention analyzing samples of *B. globigii* vegetative cells and spores, as well as the first derivative of the raw data.
Figure 6:
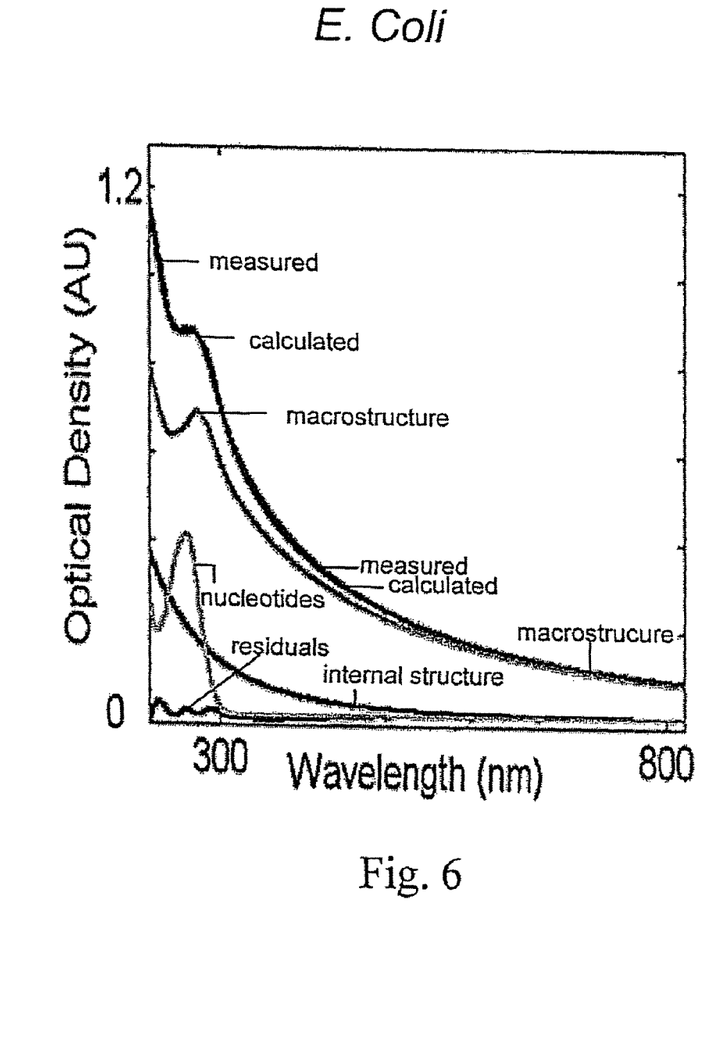
FIG. 6 is a graph of deconvoluted data for the *E. coli* raw spectrum shown in FIG. 4.
Figure 7:
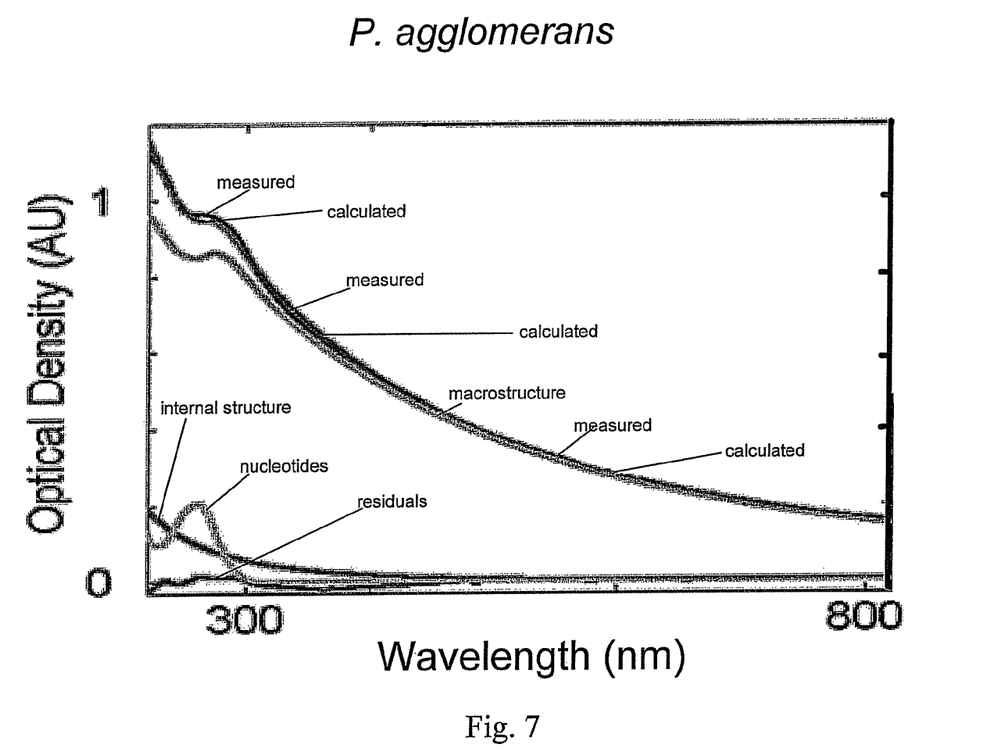
FIG. 7 is a graph of deconvoluted data for the *P. agglomerans* raw spectrum shown in FIG. 4.
Figure 8:
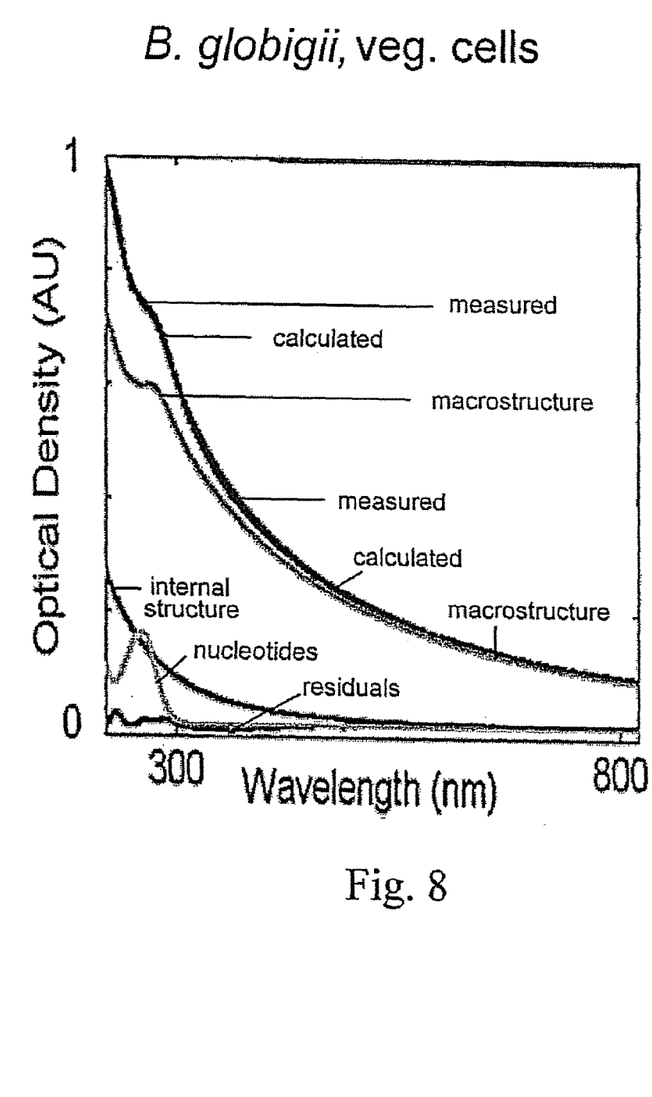
FIG. 8 is a graph of deconvoluted data for the *B. globigii* vegetative cells raw spectrum shown in FIG. 4 and FIG. 5.
Figure 9:
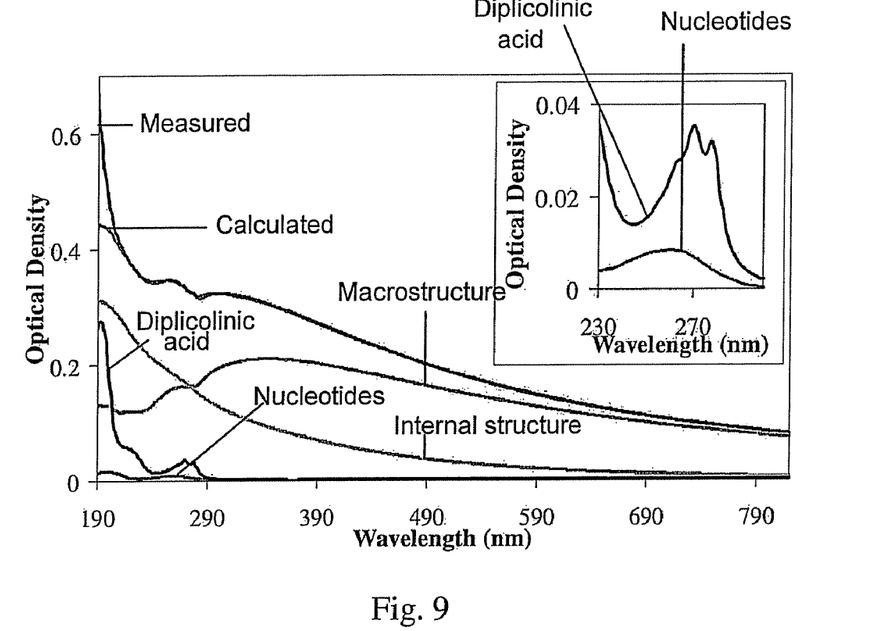
FIG. 9 is a graph of deconvoluted data for the *B. globigii* spores raw spectrum shown in FIG. 5.
Figure 10:
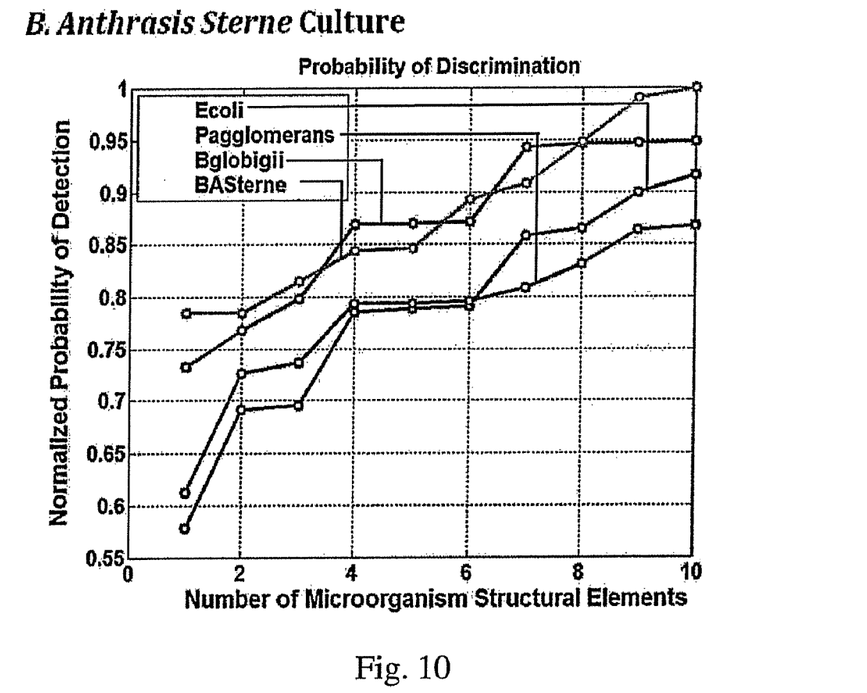
FIG. 10 is a graph illustrating the final output of deconvoluted data for *E. coli, P. agglomerans, B. globigii,* and *B. anthracis* Sterne.

An illustrative prototype of device 10 is shown in FIG. 3. The prototype device 310 has a sample inlet port 312 which is in fluid communication with a sample container, 314. Tubing 316 connects the sample inlet port 312 to a pump 318. Tubing 320, 322 connects pump 318 to a flow cell 324. The flow cell shown is a non-limiting embodiment of a common, commercially available quartz flow cell. The flow cell 324 is optically connected to a UV-VIS light source and a spectrometer, not shown. Tubing 330 and a valve 334 are connected to a filter 336. Tubing 342, 343 connects the filter 336 to a valve 344, and tubing 345 connects valve 344 to a waste outlet 346 and a waste container 348.

A first diluent inlet port 350 is in fluid communication with a diluent container 352. Tubing 354 connects port 350 to a pump 356. Tubing 358 connects pump 356 to tubing 322, 320 through a t-connector 321. Tubing 322 puts the first diluent inlet port 350 in fluid communication with the flow cell 324 and filter 336, as discussed above.

A second diluent inlet port 360 is in fluid communication with diluent container 352, and further to a pump 364 through tubing 362. Pump 364 is connected to tubing 342, 343 through tubing 366 by a t-connector 347, placing the second diluent inlet port 360 in fluid communication with the filter 336 and flow cell 324, as discussed above.

The device 310 is connected to commercially available software adapted to operate the pumps and valves in the desired sequence. The software is further adapted to analyze the data gathered by the spectrometer, as is well known in the art.

EXAMPLE

T Agar Plate Preparation: Nutrient agar was prepared by dissolving 24.8 g Difco Nutrient Agar 1.5% (Ref. 269100, Difco Laboratories, Detroit, Mich.) in 800 mL deionized water, and the solution was autoclaved for 15 minutes using a Market Forge Industries, Inc. Sterilmatic autoclave to sterilize the agar. The solution vessel cap was tightened and the vessel was inverted several times to ensure complete mixing. The vessel containing the nutrient agar was placed in a Precision Circulating Water Bath set at 50° C., to allow adequate cooling. Once the nutrient agar reached temperature, the solution was poured into Fisher sterilized disposable plastic Petri dishes (100×15 mm), enough to cover the entire bottom of the dish, and allowed to set.

Growth Media Preparation: Nutrient broth was prepared according to manufacturers' recommendations (Ref. 234000, Difco Laboratories, Detroit, Mich.) in a 2 L Erlenmeyer flask containing a magnetic stir bar. Schaeffer's Nutrient Base was prepared by adding 16.0 g Difco Laboratories Nutrient broth, 2.0 g potassium chloride and 244 mg magnesium sulfate to 1 L deionized water. This solution was placed into a 2 L Erlenmeyer flask containing a magnetic stir bar. Sponge plugs were inserted into the mouths of the vessels and capped with an SST closure purchased from Bellco Glass Inc (Cat. No. 2005-00038). The solutions were autoclaved in the Sterilmatic autoclave for 15 minutes, and then allowed to cool to room temperature before use.

Stock solutions of 10% glucose, 0.1M $MnSO_4$, 0.001M $FeSO_4$, and 1.0M $Ca(NO_3)_2$ were added to the cooled Schaeffer's Nutrient Base in volumes of 10 ml, 1 ml, 1 ml, and 1 ml respectively. ACS certified chemicals used for preparation of the stock solutions were obtained from Fisher Scientific and prepared with deionized water, and filter sterilized using a 0.22 μm Acrodisc filter and a disposable 60 cc syringe.

Cell Preparation and Culturing: *Bacillus globigii* was used for analysis of bacterial vegetative cells. *B. subtilis* was deposited as *B. globigii* and was obtained from the American Type Culture Collection, ATCC number 31028, PO Box 1549, Manassas, Va., 20108. The cells were streaked onto a nutrient agar plate and incubated overnight at 30° C. Two colonies were harvested using a Fisherbrand 10 ul steriloop and collected in a Falcon tube containing 10 ml of nutrient broth. Solution was vortexed and the cells were grown overnight at 31° C. in an incubator. The procedure was repeated using the Schaeffer's Media.

Heating strips were attached to the flasks containing Nutrient Broth and Schaeffer's Media, and then placed on stir plates with a stir speed capable of producing a vortex in the liquid. Collection probes from the NOVA Biomedical BioProfile 250 system and temperature probes from the temperature controller, Fisher Scientific, Cat # 11-463-46F, were inserted into the flasks in a manner that did not disrupt the stirring action. A 1-ml sample of vegetative cells from each of the overnight inoculants was collected and reserved for plate culturing. The remaining overnight inoculants were used to start the 1 liter growth cultures. From this point forward, samples from both Nutrient Broth and Schaeffer's media cell culture vessels were collected every hour beginning with hour zero and continuing through hour 11 for various analyses. A final sample was collected at hour 26 from each of the growth cultures. NOVA sampling was conducted every half hour, plate culturing every hour.

NOVA Analysis: Half-hour quantitative determinations of sodium, potassium, ammonium, glucose, glutamate, glutamine, pH, $PCO_2$, $PO_2$, and cell density were obtained on the NOVA Biomedical BioProfile 250 analyzer used in conjunction with the On-Line Autosampler. From the directly measured results, the calculated results are bicarbonate level, Total Carbon Dioxide, Air Saturation, and $CO_2$ Saturation.

The following prior art method analyses were conducted:

Plate Cultures: Beginning with the overnight inoculants, 1-ml samples were collected from both the Nutrient Broth and Schaeffer's media cell cultures hourly beginning at hour zero through hour 11 and another at hour 26. Serial dilutions were generated using phosphate buffer prepared from Fisher ACS Certified monobasic potassium phosphate and dibasic potassium phosphate and deionized water. Three 25-ul aliquots from each dilution were plated on quadrants on nutrient agar plates. The plates were then placed in an incubator set at 30° C. Resulting colonies were counted the following day using a Leica Quebec Darkfield Colony Counter, and cell density was calculated for comparison with the NOVA data.

HP UV-VIS Cell Density: Four milliliter samples from both the Nutrient Broth and Schaeffer's media cell cultures were collected hourly beginning with hour 2 and placed in disposable 1-cm pathlength cuvettes. The TV-VIS spectra of the samples were recorded using a diode array spectrophotometer (HP 8453A Hewlett-Packard, Palo Alto, Calif.) to determine cell density. All measurements were conducted at room temperature. Prior to analyzing each sample, the instrument was zeroed to account for any stray light.

Centrifugation: 10 ml samples from both the Nutrient Broth and Schaeffer's media cell cultures were collected hourly in 15 ml Falcon polystyrene conical tubes (Ref. 352073, Becton Dickinson, Franklin Lakes, N.J.), beginning at hour 4 and ending at hour 9. The Falcon tubes containing the samples were placed in a Fisher Scientific Centrifuge Model 225, and spun for 5 minutes at 8,000 RPM. The Falcon tubes were removed from the centrifuge, and the growth media supernatants were slowly removed using disposable plastic pipettes taking care not to disturb the cells at the bottom of the tube. The remaining cells were re-suspended in 10 ml deionized water, vortexed for a few seconds and centrifuged at 8000 rpm for 5 minutes. The water was removed in the same manner as the growth media supernatant and the cells were washed two more times with deionized water, removing the final wash water. After the final washing, the clean cells were re-suspended in 4 ml deionized water, which was also used to dilute the samples. The samples were placed in a 1 cm pathlength quartz cuvette, and the concentration was adjusted to allow for an optimal HP UV-VIS reading between 0.8 and 1.2 Absorbance Units (Au).

The culturing and analysis was repeated by the same method for *E. coli, P. agglomerans* and *B. anthracis* Sterne.

The following analyses were conducted with the filtration module of the present invention for each sample:

10 mL samples from both the Nutrient Broth and Schaeffer's media cell cultures were collected hourly, beginning at hour 2 and terminating at hour 11, with additional samples taken at hour 26. These samples were processed using the filtration module of the present invention, as illustrated in FIG. 3 to provide clean cells for pathogen identification and classification. The filtration module also possessed sterile Durapore PVDF syringe-driven filters (Millipore Corp, Bedford, Mass.) for processing the cells. The cells were first passed through a 5.00-um×25-mm filter (Millex-SV, Ref. SLSVR25LS) to filter out larger particles and then the cells were collected onto a 0.25-um×25-mm filter (Millex-GV, Ref. SLGVR25LS). The cells were washed and then delivered to a 1-cm pathlength quartz flow cell where the light scattering and absorption components were obtained using a modified Ocean Optics spectrophotometer. The light source for this spectrophotometer was a Heraeus FiberLight (Heraeus Noblelight GmbH, Germany) equipped with an optical fiber (600 um diameter) and a SMA 905 connector for coupling to the optical fiber. This 12-V deuterium and tungsten miniature UV-VIS light source is capable of producing a spectral distribution of 200-1100 nm.

HP UV-VIS Analysis of Filtered Cells:

After analysis of the cleaned cells had been performed with the Ocean Optics spectrophotometer, they were analyzed using the HP diode array spectrophotometer for comparison. Analyses were performed as described in the cell density section. Prior to running each set of samples, the spectrophotometer was zeroed to account for any stray light. A background spectrum of the quartz cuvette containing deionized water was taken. The level of dilution of each sample was selected to yield optical density values between 0.8 and 1.2 Au at 220 nm. The quartz cuvette was rinsed with copious amounts of water between each sample analysis.

The raw spectra for *E. coli, P. agglomerans* and *b. globigii*, vegetative cells are given in FIG. 4. The spectra are overlaid to illustrate the optical differences between the organisms depicted in the raw optical spectra, which are even more dramatic in the first derivative of the raw spectra.

Raw spectra for *b. globigii*, both vegetative cells and spores are given in FIG. 5, illustrating the ability to distinguish both spores and vegetative cells within a mixed culture.

The UV-VIS and light scattering raw spectra obtained by the filtration module were deconvoluted by software adapted to analyze and identify the cell, or analyte present in the sample. FIGS. 6 through 9 illustrate the contribution of the listed elements determined by the deconvolution, for *E. coli, p. agglomerans, B. globigii* vegetative cells and spores, respectively. FIG. 10 illustrates the final output of the deconvolution. The b. a. Sterne culture is correctly identified by the software by the $10^{th}$ structural element of classification.

Table 1 illustrates estimated values obtained by the present method versus literature values.

TABLE 1

| Microorganism | E. coli | B. globigii veg. cells | B. globigii spores | P. agglomerans | B. subtilis spores |
|---|---|---|---|---|---|
| Volume, $\mu m^3$ | 1.26 | 1.23 | 0.782 | 0.43 | 0.59 |
| Literature values | (1-7) | (0.51-1.5) | <1 | (0.09-1.57) | (0.76-1.00) |
| Equivalent diameter, $\mu m$ | 1.34 | 1.33 | 1.14 | 0.93 | 1.04 |
| DNA + RNA content, g/cell | $7.7 \times 10^{-14}$ | $3.64 \times 10^{-14}$ | $1.52 \times 10^{-14}$ | $2.02 \times 10^{-14}$ | $16.84 \times 10^{-16}$ |
| Literature values | ($7.0 \times 10^{-14}$) | — | — | — | ($17.1$-$121 \times 10^{-16}$) |
| DPA, % | — | — | 6.22 | — | 3.1 |
| (% dry cell (Murrell, 1969)) | | | (5.6-13.55) | | (7.14-9.3) |

Having described the invention in detail, those skilled in the art will appreciate that modifications may be made of the invention without departing from its' spirit and scope. Therefore, it is not intended that the scope of the invention be limited to the specific embodiments described. Rather, it is intended that the appended claims and their equivalents determine the scope of the invention.

What is claimed is:

1. A device comprising:
    sampling means for introducing a sample solution into the device, the sample solution containing an analyte and interfering particulate matter, wherein the particulate matter is smaller in size than the analyte;
    integral filtering means sized to segregate the analyte by preventing the analyte from passing through the filter while allowing the interfering particulate matter to pass through the filter;
    diluting means for introducing a diluent into the device to mix with the segregated analyte to form an analyte suspension for analysis, the diluting means including means to pump the diluent through the integral filtering means in a first direction to wash the segregated analyte, and means to pump the diluent through the integral filtering device in a second direction opposite to the first direction, whereby the segregated analyte is mixed with the diluent to form the analyte suspension;
    spectrometer means to analyze the analyte suspension;
    a processing unit adapted to control the sampling means, diluting means and spectrometer means; and
    a waste removal means to remove the sample solution, diluent and analyte suspension from the device.

2. The device of claim 1 wherein the sampling means comprises a sample container in fluid communication with a sample inlet port, and a peristaltic pump to pump the sample solution from the sample container through the sample inlet port into the device.

3. The device of claim 1 wherein the waste removal means comprises a waste outlet port in fluid communication with a waste container.

4. The device of claim 1 wherein the integral filtering means is a micro-pore filter.

5. The device of claim 1 wherein the diluting means comprises a diluent container in fluid communication with a first diluent inlet port, and a first diluent inlet port peristaltic pump to pump the diluent from the diluent container through the first diluent inlet port into the apparatus; and a second diluent inlet port, and a second diluent inlet port peristaltic pump to pump the diluent from the dilutent container through the second diluent inlet port into the apparatus.

6. The device of claim 1 wherein the spectrometer means comprises a light source and a spectrophotometer.

7. The device of claim 6 wherein the light source is an ultraviolet-visible light spectrum light source.

8. The device of claim 1 further including a mixing chamber to mix the segregated analyte with the diluent to form the analyte suspension.

9. An apparatus comprising:
    a sample inlet port in fluid communication with a sample container;
    an integral filter sized to segregate an analyte by preventing the analyte from passing through the filter while allowing interfering particulate matter to pass through the filter, the filter having a first side and a second side;
    a first peristaltic pump for pumping a sample from the sample container through the sample inlet port into the device and through the filter, the sample containing an analyte and interfering particulate matter, wherein the particulate matter is smaller in size than the analyte;
    a first diluent inlet port in fluid communication with a diluent container, and further in fluid communication with the integral filter;
    a second peristaltic pump for pumping diluent from the diluent container into and through the first diluent inlet port and through the filter, wherein the diluent is pumped through the filter in the first direction, whereby the segregated analyte is washed by the diluent;
    a second diluent inlet port in fluid communication with the diluent container, and further in fluid communication with the integral filter;
    a third peristaltic pump for pumping diluent from the diluent container into the apparatus through the second diluent inlet port, wherein the diluent is pumped through the filter in a second direction opposite to the first direction, whereby the segregated analyte is mixed with the diluent to form an analyte suspension;
    a flow cell for housing the analyte suspension for analysis;
    a light source and a spectrophotometer in communication with the flow cell for analyzing the analyte suspension;
    a processing unit adapted to control the first, second and third peristaltic pumps, and the light source and spectrophotometer; and
    a waste outlet port to remove the sample solution, diluent and analyte suspension from the device.

10. The apparatus of claim 9, further including:
    a first valve located between the filter and the flow cell; and
    a second valve located adjacent to the waste outlet.

11. A method comprising:
    introducing a sample solution containing an analyte and interfering particulate matter, wherein the particulate matter is smaller in size than the analyte;

integrally filtering the sample through an integral filter in a first direction to segregate the analyte from the interfering particulate matter;

forming a suspension of the analyte in a diluent by flowing the diluent through the integral filter in a second direction opposite to the first direction; and analyzing the analyte suspension with a spectrometer.

12. The method of claim 11, wherein the spectrometer is a UV-VIS spectrometer.

13. The method of claim 11 wherein the sample solution is blood or urine.

14. A method comprising:

introducing a sample solution containing an analyte and interfering particulate matter, wherein the particulate matter is smaller in size than the analyte into a portable device;

passing the sample solution through an integral filter in a first direction, the filter being sized to segregate the analyte by preventing the analyte from passing through the filter while allowing the interfering particulate matter to pass through the filter;

introducing a diluent into the device;

flowing the diluent through the filter in a second direction opposite to the first direction thereby mixing the diluent with the segregated analyte to form an analyte suspension;

housing the analyte suspension in a quartz flow cell; and analyzing the analyte suspension with a spectrometer to produce an optical spectrum.

15. The method of claim 14 further including controlling the device with software adapted to operate the spectrometer.

16. The method of claim 14 further including deconvoluting the optical spectrum with software adapted to deconvolute and identify the analyte.

17. The method of claim 14, wherein the spectrometer is a UV-VIS spectrometer.

18. The method of claim 14 wherein the sample solution is blood or urine.

* * * * *